(12) United States Patent
Tang et al.

(10) Patent No.: US 6,384,278 B1
(45) Date of Patent: May 7, 2002

(54) BORON-MEDIATED AMIDATION OF CARBOXYLIC ACIDS

(75) Inventors: Pingwah Tang, Elmsford; Feng Ye, Ossining, both of NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 09/778,047

(22) Filed: Feb. 5, 2001

Related U.S. Application Data

(60) Provisional application No. 60/180,259, filed on Feb. 4, 2000.

(51) Int. Cl.[7] .................. C07C 233/00; C07C 231/00
(52) U.S. Cl. .................. 564/123; 564/133; 564/134; 564/135; 564/136; 564/138; 564/139; 564/141; 564/142; 564/199; 564/200
(58) Field of Search ................. 564/138, 136, 564/139, 133, 134, 135, 141, 142, 123, 199, 200

(56) References Cited

U.S. PATENT DOCUMENTS 5,773,647 A 6/1998 Leone-Bay et al. ......... 562/444

OTHER PUBLICATIONS

Trapani et al., Synthesis; vol. 12 (1983), pp. 1013–1014.*
"Trimethylamine–Borane as Useful Reagent in the N–Acylation or N–Alkylation of Amines by Carboxylic Acids"; Giuseppe Trapani, Antonia Reho, Andrea Latrofa; *Synthesis International Journal of Methods of Synthetic Organic Chemistry*, 12:1013 (Dec. 1983).

"A Convenient Method of Amidation of Carboxlic Aids Using Boron Tifluroide Etherate"; Junichi Tani, Toyonari Oine, Ichizo Inoue; *Synthesis International Journal of Methods of Synthetic Organic Chemistry*, 11:714 (Nov. 1975).

"Some Amide Forming Reactions Involving Boron Reagents"; A. Pelter, T.E. Levitt and P. Nelson; *Tetrahedron.* vol. 26, pp. 1539–1544, Pergamon Press 1970.

"A New Synthesis of Amides and Macrocyclic Lactams"; David B. Collum, Shen–Chu Chen, Bruce Ganem, *The Journal of Organic Chemistry;* vol. 43, No. 22, Oct. 27, 1978.

"3,4,5–Trifluorobenzeneboronic Acid as an Extremely Active Amidation Catalyst"; *The Journal of Organic Chemistry;* vol. 61, No. 13, Jun. 28, 1996.

* cited by examiner

*Primary Examiner*—Samuel Barts
*Assistant Examiner*—Elvis O. Price
(74) *Attorney, Agent, or Firm*—Darby & Darby

(57) ABSTRACT

The present invention provides an inexpensive one-step method for preparing an aromatic carboxamide, such as a phenyl substituted carboxamide) by reacting an aromatic amine (e.g. a phenylamine) and a carboxylic acid (e.g. an alkanoic acid or ester thereof) in the presence of a boron containing compound (e.g. boronic acid or boric acid) and, optionally, a chelating agent (e.g. a 2-pyridinylamine).

60 Claims, No Drawings

BORON-MEDIATED AMIDATION OF CARBOXYLIC ACIDS

This application claims the benefit of U.S. Ser. No. 60/180,259 filed Feb. 4, 2000, which is hereby incorporated by reference.

FIELD OF THE INVENTION

The present invention relates to a method of amidating carboxylic acids with an aromatic amine in the presence of a boron containing compound, such as boric acid, and, optionally, a 2-pyridinylamine.

BACKGROUND OF THE INVENTION

Carboxamides, such as those disclosed in U.S. Pat. No. 5,773,647, have been found to be highly effective as delivery agents for active agents, particularly for oral administration of active agents.

Generally, carboxamides are prepared by an amidation reaction between a carboxylic acid and an amine. The carboxylic acid is typically converted into an electrophilic intermediate, usually an acid chloride. The acid chloride is then reacted with the amine in the presence of an activating agent. Many acid chlorides, however, are unstable or are not compatible with other functional groups present in the acid or amine. Therefore, protection and deprotection steps must be performed in order to stabilize the intermediate and protect various functional groups. This dramatically increases the cost of preparing the carboxamide.

Carboxamides may also be formed by reacting a carboxylic acid with 1-hydroxybenzotriazole in the presence of coupling agents, such as 1,3-dicyclohexylcarbodiimide (DCC) and ethylene dichloride (EDC). This method, however, forms urea byproducts which are often difficult to remove, especially in large scale preparations.

Boron trifluoride etherate, trialkylboranes, trialkoxyboranes, catecholborane, and arylboronic acids have also been reported to catalyze amidation reactions of carboxylic acids. See, for example, Trapani, G. et al., *Synthesis*, 1013 (1983); Tani, J. et al., *Synthesis*, 714 (1975); Pelter, A. et al., *Tetrahedron*, 26:1539 (1970); Collum, D. B. et al., *J. Org. Chem.*, 43:4393 (1978); Ishihara, K. et al., *J. Org. Chem.*, 61:4196 (1996).

Therefore, there is a need for an inexpensive and simple method for preparing carboxamides from carboxylic acids.

SUMMARY OF THE INVENTION

The present invention provides an inexpensive one-step method for preparing an aromatic carboxamide, such as a phenyl substituted carboxamide by reacting an aromatic amine (e.g. a phenylamine) and a carboxylic acid (e.g. an alkanoic acid or ester thereof) in the presence of a boron containing compound (e.g. boronic acid or boric acid) and, optionally, a chelating agent (e.g. a 2-pyridinylamine).

A preferred embodiment is a method for preparing a carboxamide having the formula

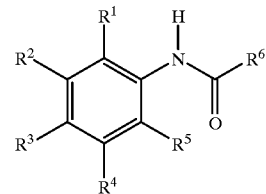

where $R^1$, $R^2$, $R^3$, $R^4$, and $R^5$ are independently hydrogen, —OH, —O—$R^7$, substituted or unsubstituted alkyl, substituted or unsubstituted alkenyl, substituted or unsubstituted alkoxy, substituted or unsubstituted aryl, carboxyl, substituted or unsubstituted alkoxycarbonyl, halogen, nitrile, —OC(O)CH$_3$, —SO$_3$H, or —NR$^{13}$R$^{14}$;

$R^6$ is $C_1$–$C_{12}$ alkyl;

$R^6$ is optionally substituted with one or more alkenyl, alkoxycarbonyl, carboxyl, —OH, or halogen;

$R^7$ is hydrogen, alkyl, or aryl; and $R^{13}$ and $R^{14}$ are independently hydrogen, $C_1$–$C_4$ alkyl, or oxygen.

The method comprises the step of reacting (a) an aromatic amine having the formula

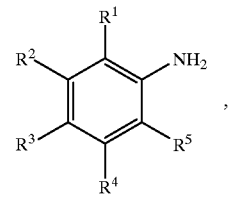

with (b) an acid having the formula $R^6$—COOH in the presence of a boron containing compound and, optionally, a chelating agent to form the carboxamide, where $R^1$, $R^2$, $R^3$, $R^4$, $R^5$, and $R^6$ are defined as above. A preferred acid has the formula

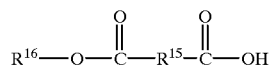

where $R^{15}$ is a $C_1$–$C_{12}$ alkyl and $R^{16}$ is an alkyl (e.g. a $C_1$–$C_3$ alkyl). A preferred chelating agent is a 2-pyridinylamine. Preferably the boron containing compound is boric acid and the 2-pyridinylamine is 2-amino-5-picoline. The carboxamide may be subsequently modified to include a carboxylic acid terminal on the $R^6$ group, if it does not already have such a terminal.

A more preferred embodiment is a method for preparing a carboxamide having the formula:

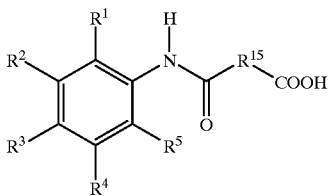

where
- $R^1$, $R^2$, $R^3$, $R^4$, and $R^5$ are independently hydrogen, —OH, —O—$R^7$, substituted or unsubstituted alkyl, substituted or unsubstituted alkenyl, substituted or unsubstituted alkoxy, substituted or unsubstituted aryl, carboxyl, substituted or unsubstituted alkoxycarbonyl, halogen, nitrile, —OC(O)CH$_3$, —SO$_3$H, or —NR$^{13}$R$^{14}$;
- $R^7$ is hydrogen, alkyl, or aryl;
- $R^{13}$ and $R^{14}$ are independently hydrogen, $C_1$–$C_4$ alkyl, or oxygen; and
- $R^{15}$ is $C_1$–$C_{12}$ alkyl.

The method comprises the steps of (i) reacting (a) an aromatic amine having the formula

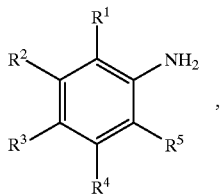

with (b) an acid having the formula

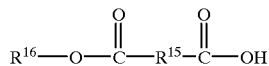

where $R^{15}$ is a $C_1$–$C_{12}$ alkyl and $R^{16}$ is an alkyl (e.g. a $C_1$–$C_3$ alkyl), in the presence of a boron containing compound and, optionally, a chelating agent to form an intermediate having the formula

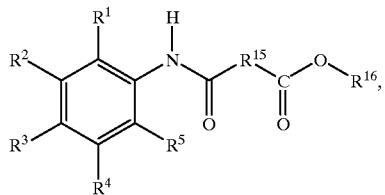

where $R^1$, $R^2$, $R^3$, $R^4$, $R^5$, $R^{15}$, and $R^{16}$ are defined as above; and (ii) hydrolyzing the intermediate to form the final carboxamide. Preferably, the boron containing compound is boric acid and the chelating agent is a 2-pyridinylamine, such as a 2-amino-5-picoline.

DETAILED DESCRIPTION OF THE INVENTION

The alkyl, alkenyl, alkoxy and aryl groups of $R^1$, $R^2$, $R^3$, $R^4$, and $R^5$ may be substituted with, for example, —OH, F, and alkyl and aryl groups. $R^1$, $R^2$, $R^3$, $R^4$, and $R^5$ may be $C_1$–$C_{18}$ alkyl, $C_2$–$C_{18}$ alkenyl, $C_1$–$C_{18}$ alkoxy, or ($C_1$–$C_{18}$ alkoxy)carbonyl. For example, $R^1$, $R^2$, $R^3$, $R^4$, and $R^5$ maybe $C_1$–$C_4$ alkyl, $C_2$–$C_4$ alkenyl, or $C_1$–$C_4$ alkoxy. The alkoxycarbonyl group of $R^1$, $R^2$, $R^3$, $R^4$, and $R^5$ may be substituted with, for example, alkyl groups (such as $C_1$–$C_4$ alkyl).

Suitable boron containing compounds include, but are not limited to, boronic acids, such as those having the formula $R^8$—B(OH)$_2$, where $R^8$ is —OH; aryl; $C_1$–$C_8$ alkyl, optionally substituted with $C_1$–$C_3$ alkyl; or a polymer. Preferably, the boron containing compound is boric acid, i.e., $R^8$ is —OH.

Without being bound by any theory, the inventors believe that boric acid forms a reactive complex with the carboxylic acid to form an acyloxyboron intermediate and water. After the water is removed, the acyloxyboron intermediate readily reacts with the aromatic amine to afford the desired carboxamide and regenerate boric acid, the amidation catalyst.

The chelating agent may be any chelating agent known in the art. Suitable chelating agents include, but are not limited to, electron donating chelating agents. Preferred chelating agents include, but are not limited to, 2-pyridinylamines. Suitable 2-pyridinylamines include, but are not limited to, those having the formula

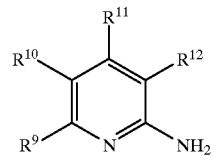

where $R^9$, $R^{10}$, $R^{11}$, and $R^{12}$ are independently hydrogen, substituted or unsubstituted $C_1$–$C_4$ alkyl, or substituted or unsubstitued aryl. The alkyl and aryl groups of $R^9$, $R^{10}$, $R^{11}$, and $R^{12}$ may be substituted with, for example, alkyl (such as $C_1$–$C_4$ alkyl) and aryl groups. Preferably, the 2-pyridinylamine is 2-amino-4-picoline, 2-amino-5-picoline, 2-amino-6-picoline, 2-amino-4,6-dimethylpyridine, or any combination of any of the foregoing. More preferably, the 2-pyridinylamine is 2-amino-5-picoline.

The boron containing compound and, optionally, the 2-pyridinylamine catalyze the reaction between the aromatic amine and the acid. Without being bound to any theory, the inventors believe that the boron containing compound forms a complex with the 2-pyridinylamine. This complex may react with the acid to form an acyloxyboron intermediate which can readily react with the aromatic amine to yield the carboxamide.

The reaction may be performed at a temperature of from about 20° C. to about 200° C. The reaction may be performed in the solid or liquid phase.

The aromatic amine and acid are preferably dissolved in a solvent. Suitable solvents include, but are not limited to, aromatic solvents, such as benzene, xylene, mesitylene, and toluene; hydrocarbon solvents, such as hexane and octane; and any combination of any of the foregoing. Preferably, the solvent is toluene.

Water which is formed as a byproduct from the reaction of the aromatic amine and the acid is preferably removed during the reaction, such as, with a Dean-Stark separator.

The reaction is typically performed at atmospheric pressure. Preferably, the reaction is carried out under an inert gas blanket, such as nitrogen or argon.

The molar ratio of aromatic amine to the acid preferably ranges from about 1:1 to about 1:1.1 and more preferably from about 1:1 to about 1:1.03. The molar ratio of boron containing compound to 2-pyridinylamine preferably ranges from about 10:1 to about 1:5 and more preferably is about 1:1. The molar ratio of boron containing compound or 2-pyridinylamine to aromatic amine or acid preferably ranges from about 1:100 to about 1:1 and more preferably ranges from about 1:50 to about 1:4.

Generally, the reaction mixture contains from about 0.1 to about 4 moles of aromatic amine, from about 0.1 to about 4 moles of the acid, and from about 0.001 to about 4 moles of boron containing compound per liter of reaction mixture. The reaction mixture may optionally contain from about 0.001 moles to about 8 moles of 2-pyridinylamine per liter of reaction mixture. Preferably, the reaction mixture contains about 0.5 moles of aromatic amine per liter of reaction mixture.

The reaction may be performed by refluxing a mixture of the aromatic amine and the acid in a solvent and in the presence of the boron containing compound and 2-pyridinylamine. Preferably, the mixture contains toluene as a solvent. Typically, refluxing is performed at a temperature of from about 80 to about 150° C. and preferably at about 110° C. Typically, the mixture is refluxed for 1 to 16 hours, depending on the starting materials.

The carboxamide may be purified by any method known in the art. For example, the carboxamide may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0–500 mM sodium chloride gradient is employed.

The carboxamide may be subsequently modified to include a carboxylic acid terminal on the $R^6$ group, if it does not already have such a terminal. This may be done by any method known in the art. For example, if the acid used in the reaction has the formula

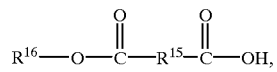

the carboxamide may be hydrolyzed to remove the $R^{16}$ group and leave a carboxylic acid group on the carboxamide. Hydrolysis may be performed by any method known in the art, such as by reacting the carboxamide (e.g. the intermediate carboxamide discussed above) with sodium hydroxide.

The following examples are intended to describe the present invention without limitation.

EXAMPLE 1

8-(5-chloro-2-hydroxyanilino)-8-oxooctanoic acid was prepared as follows. A suspension of 2 amino-4-chlorophenol (17.88 g, 124.5 mmol), 8-ethoxy-8-oxo-octanoic acid (25.19 g, 124.5 mmol), boric acid (0.385 g, 6.23 mmol), and 2-amino-5-picoline (0.675 g, 6.23 mmol) in 160 mL of dried toluene was heated at reflux (110° C.) under nitrogen for 4 hours during which water (2.5 mL) produced in the reaction was removed by azeotropic distillation in a Dean-Stark separation unit. Thin layer chromatography on silica gel with an eluant of ethylacetate and heptane at a molar ratio of 1:1 indicated the completion of the reaction. The mixture was cooled and a 2N aqueous solution of sodium hydroxide (125 mL, 250 mmol) was added. The mixture was heated at reflux (about 85° C.) for 4 hours and cooled. The cooled mixture was diluted with ethyl acetate (300 mL) and water (150 mL). The aqueous layer was washed with two portions of ethyl acetate (250 mL). After careful separation, the aqueous layer was chilled and acidified with a 10% (by weight) solution of hydrochloric acid (86.20 mL, 250 mmol) to yield a solid. The solid was filtered, washed with hexane, and dried under vacuum. Trituration with dichloromethane yielded the 8-(5-chloro-2-hydroxyanilino)-8-oxooctanoic acid (22.39 g, 60%) as an off-white solid. HPLC (Column: Higgins Kromasil 100 C18, water/acetonitile/acetic acid: 950/50/1, 3 mL/min, 220 nm) $R_t$ 5.38 min.; melting point 123–124° C.; $^1$H NMR(DMSO $d_6$, 300 MHz)δ: 1.28(m, 4H), 1.51 (m, 4H), 2.19 (t, 2H), 2.39 (t, 2H),6.83 (d, 1H), 6.93 (dd, 1H), 7.95 (d, 1H), 9.20 (s, 1H), 10.10 (s, 1H), 12.00 (br s, 1H); $^{13}$C NMR (DMSO $d_6$, 75 MHz) δ: 24.29, 24.90, 28.20, 33.58, 35.90, 116.50, 121.02, 122.20, 123.41, 127.74, 148.23, 171.93, 174.26. MS m/z 300 (M+1)$^+$. Anal. Calcd for $C_{14}H_{18}ClNO_4$: C, 56.10; H, 6.05; Cl, 11.83, N, 4.67. Found: C, 56.07, H, 6.11, 11.98, N, 4.64.

EXAMPLE 2

8-(5-chloro-2-hydroxyanilino)-8-oxooctanoic acid was prepared as follows. A suspension of 2-amino-4-chlorophenol (17.88 g, 124.5 mmol), 8-ethoxy-8-oxooctanoic acid (25.19 g, 124.5 mmol), boric acid (0.385 g, 6.23 mmol) in 150 mL of dried toluene was heated at reflux (110° C.) under nitrogen for 4 hours during which water (2.5 mL) produced in the reaction was removed by azeotropic distillation in a Dean-Stark separation unit. The reaction was observed by thin layer chromatography on silica gel (Eluant: ethylacetate:heptane 1:1). The reaction mixture was cooled in a water bath to room temperature. 2N aqueous solution of sodium hydroxide (125 mL, 250 mmol) was added to the mixture. The mixture was heated at reflux for 4 hours. The reaction mixture was cooled in a water bath to room temperature. The mixture was then diluted with ethyl acetate (300 mL) and water (150 mL). The aqueous layer was washed with two portions of ethyl acetate (250 mL). After careful separation, the aqueous layer was chilled and acidified with a 10% (by weight) solution of hydrochloric acid (86.20 mL, 250 mmol) to yield a solid which was filtered, washed with hexane, and dried under vacuum. Trituration with dichloromethane yielded the desired acid (21.75 g, 57%) as an off-white solid. HPLC (Column: Higgins Kromasil 100 C18, water/acetonitile/acetic acid: 950/50/1, 3 mL/min, 220 nm) showed one single peak. $R_t$ was 5.38 minutes.

EXAMPLE 3

5-(5-chloro-2-hydroxyanilino)-5-oxopentanoic acid was prepared by the method described in Example 1, except 5-ethoxy-5-oxo-pentanoic acid was substituted for 8-ethoxy-8-oxo-octanoic acid.

EXAMPLE 4

10-(2-hydroxyanilino)-10-oxo-decanoic acid was prepared by the method described in Example 1, except 10-ethoxy-10-oxo-decanoic acid was substituted for 8-ethoxy-8-oxo-octanoic acid.

EXAMPLE 5

8-(2-hydroxyanilino)-8-oxo-octanoic acid, 9-(2-hydroxyanilino)-9-oxo-nonanoic acid, 6-(2-hydroxy-4- methylanilino)-6-oxo-hexanoic acid, 9-(2-hydroxy-4-methylanilino)-9-oxo-nonanoic acid, 10-(2-hydroxy-4-methylanilino)-10-oxo-decanoic acid, 6-(2-hydroxy-5-methylanilino)-6-oxo-hexanoic acid, 9-(2-hydroxy-5-methylanilino)-9-oxo-nonanoic acid, 10-(2-hydroxy-5-methylanilino)-10-oxo-decanoic acid, 7-(5-chloro-2-hydroxyanilino)-7-oxo-heptanoic acid, 10-(5-chloro-2-hydroxyanilino)-10-oxo-decanoic acid, 9-(5-fluoro-2-hydroxyanilino)-7-oxo-nanonoic acid, and 10-(5-fluoro-2-hydroxyanilino)-10-oxo-decanoic acid are prepared by the method described in Example 1 using the appropriate starting materials.

All patents, publications, applications, and test methods mentioned above are hereby incorporated by reference. Many variations of the present matter will suggest themselves to those skilled in the art in light of the above detailed description. All such obvious variations are within the patented scope of the appended claims.

What is claimed is:

1. A method for preparing a carboxamide having the formula

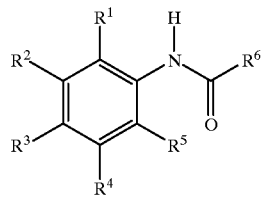

wherein $R^1$, $R^2$, $R^3$, $R^4$, and $R^5$ are independently hydrogen, —OH, —O—$R^7$, substituted or unsubstituted alkyl, substituted or unsubstituted alkenyl, substituted or unsubstituted alkoxy, substituted or unsubstituted aryl, carboxyl, substituted or unsubstituted alkoxycarbonyl, halogen, nitrile, —OC(O)CH$_3$, —SO$_3$H, or —NR$^{13}$R$^{14}$;

$R^6$ is $C_1$–$C_{12}$ alkyl;

$R^6$ is optionally substituted with one or more alkenyl, alkoxycarbonyl, carboxyl, —OH, or halogen;

$R^7$ is hydrogen, alkyl, or aryl; and $R^{13}$ and $R^{14}$ are independently hydrogen, $C_1$–$C_4$ alkyl, or oxygen, the method comprising reacting (a) an aromatic amine having the formula

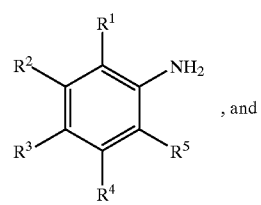

, and (b) an acid in the presence of a boron containing compound to form the carboxamide, wherein the acid has the formula

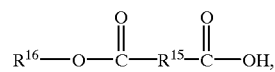

wherein $R^{15}$ is a $C_1$–$C_{12}$ alkyl and $R^{16}$ is an alkyl.

2. The method of claim 1, wherein $R^{16}$ is $C_1$–$C_3$ alkyl.

3. The method of claim 1, wherein the boron containing compound has the formula $R^8$—B(OH)$_2$, wherein $R^8$ is —OH; aryl; $C_1$–$C_8$ alkyl, optionally substituted with $C_1$–$C_3$ alkyl; or a polymer.

4. The method of claim 3, wherein the boron containing compound is boric acid.

5. The method of claim 1, wherein the molar ratio of aromatic amine to the acid ranges from about 1:1 to about 1:1.1.

6. The method of claim 5, wherein the molar ratio of aromatic amine to the acid ranges from about 1:1 to about 1:1.03.

7. The method of claim 1, wherein the molar ratio of boron containing compound to aromatic amine ranges from about 1:100 to about 1:1.

8. The method of claim 7, wherein the molar ratio of boron containing compound to aromatic amine ranges from about 1:50 to about 1:4.

9. The method of claim 1, wherein the reaction mixture comprises from about 0.1 to about 4 moles of aromatic amine, from about 0.1 to about 4 moles of the acid, and from about 0.001 to about 4 moles of boron containing compound per liter of reaction mixture.

10. The method of claim 9, wherein the reaction mixture comprises about 0.5 moles of aromatic amine per liter of reaction mixture.

11. The method of claim 1, wherein the reaction is performed in the presence of a chelating agent.

12. The method of claim 1, wherein the reaction is performed in a solvent.

13. The method of claim 12, wherein the solvent comprises an aromatic solvent, hydrocarbon solvent, or any combination of any of the foregoing.

14. The method of claim 13, wherein the solvent comprises benzene, xylene, mesitylene, toluene, hexane, octane, or any combination of any of the foregoing.

15. The method of claim 14, wherein the solvent comprises toluene.

16. The method of claim 1, further comprising purifying the carboxamide.

17. A method for preparing a carboximide having the formula

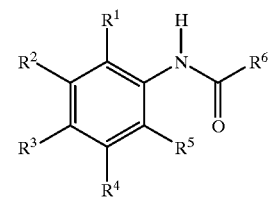

wherein $R^1$, $R^2$, $R^3$, $R^4$, and $R^5$ are independently hydrogen, —OH, —O—$R^7$, substituted or unsubstituted alkyl, substituted or unsubstituted alkenyl, substituted or unsubstituted alkoxy, substituted or unsubstituted aryl, carboxyl, substituted or unsubstituted alkoxycarbonyl, halogen, nitrile, —OC(O)CH$_3$, —SO$_3$H, or —NR$^{13}$R$^{14}$;

$R^6$ is $C_1$–$C_{12}$ alkyl;

$R^6$ is optionally substituted with one or more alkenyl, alkoxycarbonyl, carboxyl, —OH, or halogen;

$R^7$ is hydrogen, alkyl, or aryl; and $R^{13}$ and $R^{14}$ are independently hydrogen, $C_1$–$C_4$ alkyl, or oxygen, the method comprising reacting (a) an aromatic amine having the formula

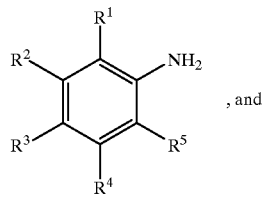

, and (b) an acid having the formula $R^6$—COOH in the presence of a boron containing compound and a 2-pyridinylamine to form the carboxamide.

18. The method of claim 17, wherein the acid has the formula

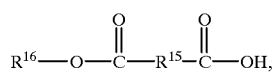

wherein $R^{15}$ is a $C_1$–$C_{12}$ alkyl and $R^{16}$ is an alkyl.

19. The method of claim 18, wherein $R^{16}$ is $C_1$–$C_3$ alkyl.

20. The method of claim 17, wherein the boron containing compound has the formula $R^8$—$B(OH)_2$, wherein $R^8$ is —OH; aryl; $C_1$–$C_8$alkyl, optionally substituted with $C_1$–$C_3$ alkyl; or a polymer.

21. The method of claim 20, wherein the boron containing compound is boric acid.

22. The method of claim 17, wherein the 2-pyridinylamine has the formula

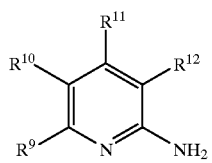

wherein $R^9$, $R^{10}$, $R^{11}$, and $R^{12}$ are independently hydrogen, substituted or unsubstituted $C_1$–$C_4$ alkyl, or substituted or unsubstitued aryl.

23. The method of claim 22, wherein the 2-pyridinylamine is 2-amino-4-picoline, 2-amino-5-picoline, 2-amino-6-picoline, 2-amino-4,6-dimethylpyridine, or any combination of any of the foregoing.

24. The method of claim 23, wherein the 2-pyridinylamine is 2-amino-5-picoline.

25. The method of claim 17, wherein the molar ratio of aromatic amine to the acid ranges from about 1:1 to about 1:1.1.

26. The method of claim 25, wherein the molar ratio of aromatic amine to the acid ranges from about 1:1 to about 1:1.03.

27. The method of claim 17, wherein the molar ratio of boron containing compound to 2-pyridinylamine ranges from about 10:1 to about 1:5.

28. The method of claim 27, wherein the molar ratio of boron containing compound to 2-pyridinylamine is about 1:1.

29. The method of claim 17, wherein the molar ratio of boron containing compound to aromatic amine ranges from about 1:100 to about 1:1.

30. The method of claim 29, wherein the molar ratio of boron containing compound to aromatic amine ranges from about 1:50 to about 1:4.

31. The method of claim 17, wherein the reaction mixture comprises from about 0.1 to about 4 moles of aromatic amine, from about 0.1 to about 4 moles of the acid, from about 0.001 to about 4 moles of boron containing compound, and from about 0.001 moles to about 8 moles of 2-pyridinylamine per liter of reaction mixture.

32. The method of claim 31, wherein the reaction mixture comprises about 0.5 moles of aromatic amine per liter of reaction mixture.

33. The method of claim 17, wherein the reaction is performed in a solvent.

34. The method of claim 33, wherein the solvent comprises an aromatic solvent, hydrocarbon solvent, or any combination of any of the foregoing.

35. The method of claim 34, wherein the solvent comprises benzene, xylene, mesitylene, toluene, hexane, octane, or any combination of any of the foregoing.

36. The method of claim 35, wherein the solvent comprises toluene.

37. The method of claim 17, further comprising purifying the carboxamide.

38. A method for preparing a carboxamide having the formula

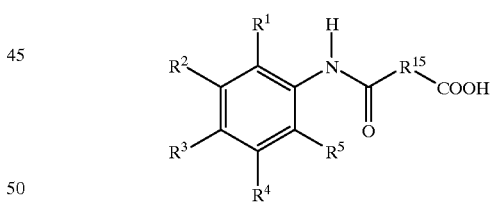

wherein $R^1$, $R^2$, $R^3$, $R^4$, and $R^5$ are independently hydrogen, —OH, —O—$R^7$, substituted or unsubstituted alkyl, substituted or unsubstituted alkenyl, substituted or unsubstituted alkoxy, substituted or unsubstituted aryl, carboxyl, substituted or unsubstituted alkoxycarbonyl, halogen, nitrile, —OC(O)$CH_3$, —$SO_3H$, or —$NR^{13}R^{14}$;

$R^7$ is hydrogen, alkyl, or aryl;

$R^{13}$ and $R^{14}$ are independently hydrogen, $C_1$–$C_4$ alkyl, or oxygen; and $R^{15}$ is $C_1$–$C_{12}$ alkyl, the method comprising:
(i) reacting (a) an aromatic amine having the formula

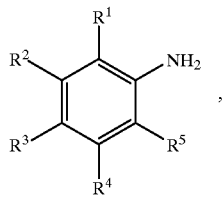

with (b) an acid having the formula

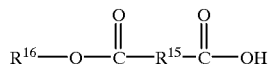

wherein $R^{15}$ is a $C_1$–$C_{12}$ alkyl and $R^{16}$ is an alkyl, in the presence of a boron containing compound and to form an intermediate having the formula

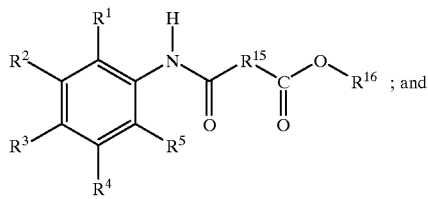

(ii) hydrolyzing the intermediate to form the carboxamide.

39. The method of claim 38, wherein $R^{16}$ is $C_1$–$C_3$ alkyl.
40. The method of claim 38, wherein the boron containing compound is boric acid.
41. The method of claim 38, wherein the reaction step is performed in the presence of a chelating agent.
42. The method of claim 41, wherein the chelating agent is a 2-pyridinylamine.
43. The method of claim 42, wherein the chelating agent is a 2-amino-5-picoline.
44. A method for preparing a phenyl substituted carboxamide comprising reacting (a) an aromatic amine and (b) an alkanoic acid or ester thereof in the presence of a boron containing compound, wherein a chelating agent is present during the reaction step.
45. A method for preparing a carboxamide having the formula

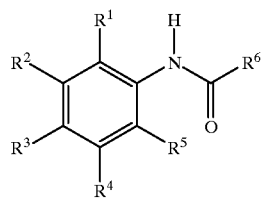

wherein
$R^1$, $R^2$, $R^3$, $R^4$, and $R^5$ are independently hydrogen, —OH, —O—$R^7$, substituted or unsubstituted alkyl, substituted or unsubstituted alkenyl, substituted or unsubstituted alkoxy, substituted or unsubstituted aryl, carboxyl, substituted or unsubstituted alkoxycarbonyl, halogen, nitrile, —OC(O)CH$_3$, —SO$_3$H, or —NR$^{13}$R$^{14}$;
$R^6$ is $C_1$–$C_{12}$ alkyl;
$R^6$ is optionally substituted with one or more alkenyl, alkoxycarbonyl, carboxyl, —OH, or halogen;

$R^7$ is hydrogen, alkyl, or aryl; and
$R^{13}$ and $R^{14}$ are independently hydrogen, $C_1$–$C_4$ alkyl, or oxygen,
the method comprising reacting
(a) an aromatic amine having the formula

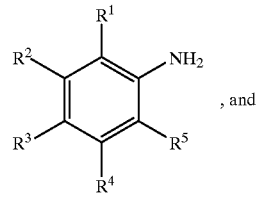

(b) an acid having the formula $R^6$—COOH
in the presence of a boron containing compound to form the carboxamide, wherein the boron containing compound has the formula $R^8$—B(OH)$_2$, wherein $R^8$ is —OH; aryl; $C_1$–$C_8$ alkyl, optionally substituted with $C_1$–$C_3$ alkyl; or a polymer.
46. The method of claim 45, wherein the acid has the formula

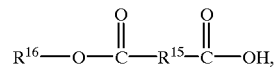

wherein $R^{15}$ is a $C_1$–$C_{12}$ alkyl and $R^{16}$ is an alkyl.
47. The method of claim 46, wherein $R^{16}$ is $C_1$–$C_3$ alkyl.
48. The method of claim 45, wherein the boron containing compound is boric acid.
49. The method of claim 45, wherein the molar ratio of aromatic amine to the acid ranges from about 1:1 to about 1:1.1.
50. The method of claim 49, wherein the molar ratio of aromatic amine to the acid ranges from about 1:1 to about 1:1.03.
51. The method of claim 45, wherein the molar ratio of boron containing compound to aromatic amine ranges from about 1:100 to about 1:1.
52. The method of claim 51, wherein the molar ratio of boron containing compound to aromatic amine ranges from about 1:50 to about 1:4.
53. The method of claim 45, wherein the reaction mixture comprises from about 0.1 to about 4 moles of aromatic amine, from about 0.1 to about 4 moles of the acid, and from about 0.001 to about 4 moles of boron containing compound per liter of reaction mixture.
54. The method of claim 53, wherein the reaction mixture comprises about 0.5 moles of aromatic amine per liter of reaction mixture.
55. The method of claim 45, wherein the reaction is performed in the presence of a chelating agent.
56. The method of claim 45, wherein the reaction is performed in a solvent.
57. The method of claim 56, wherein the solvent comprises an aromatic solvent, hydrocarbon solvent, or any combination of any of the foregoing.
58. The method of claim 57, wherein the solvent comprises benzene, xylene, mesitylene, toluene, hexane, octane, or any combination of any of the foregoing.
59. The method of claim 58, wherein the solvent comprises toluene.
60. The method of claim 45, further comprising purifying the carboxamide.

* * * * *